US009011941B2

(12) United States Patent
Jones et al.

(10) Patent No.: US 9,011,941 B2
(45) Date of Patent: *Apr. 21, 2015

(54) COMBINED ALLERGY TREATMENT AND ANTI-DRYING COMPOSITIONS AND RELATED METHODS

(71) Applicant: Xlear Inc., Orem, UT (US)

(72) Inventors: Alonzo H. Jones, Plainview, TX (US); Nathan Jones, Orem, UT (US)

(73) Assignee: Xlear, Inc., Orem, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/258,993

(22) Filed: Apr. 22, 2014

(65) Prior Publication Data

US 2014/0228304 A1 Aug. 14, 2014

Related U.S. Application Data

(63) Continuation of application No. 13/903,860, filed on May 28, 2013, now Pat. No. 8,709,508.

(60) Provisional application No. 61/651,741, filed on May 25, 2012.

(51) Int. Cl.

| *A01N 65/00* | (2009.01) |
| *A61K 31/7004* | (2006.01) |
| *A61K 9/00* | (2006.01) |
| *A61K 36/28* | (2006.01) |
| *A61K 36/53* | (2006.01) |
| *A61K 45/06* | (2006.01) |
| *A61K 31/137* | (2006.01) |
| *A61K 31/353* | (2006.01) |
| *A61K 31/4174* | (2006.01) |
| *A61K 31/55* | (2006.01) |
| *A61K 31/58* | (2006.01) |
| *A61K 47/26* | (2006.01) |
| *A61K 9/08* | (2006.01) |

(52) U.S. Cl.
CPC ........... *A61K 31/7004* (2013.01); *A61K 9/0043* (2013.01); *A61K 36/28* (2013.01); *A61K 36/53* (2013.01); *A61K 45/06* (2013.01); *A61K 31/137* (2013.01); *A61K 31/353* (2013.01); *A61K 31/4174* (2013.01); *A61K 31/55* (2013.01); *A61K 31/58* (2013.01); *A61K 47/26* (2013.01); *A61K 9/08* (2013.01)

(58) Field of Classification Search
None
See application file for complete search history.

(56) References Cited

U.S. PATENT DOCUMENTS 6,054,143 A * 4/2000 Jones ........................... 424/434

* cited by examiner

*Primary Examiner* — Michael Meller
(74) *Attorney, Agent, or Firm* — Phillips Ryther & Winchester; Matthew D. Thayne

(57) ABSTRACT

Compositions and methods for alleviating an allergy condition while also reducing a drying effect of an allergy treatment composition or another anti-mucosal composition. In some embodiments and implementations, a composition may be provided comprising an allergy treatment composition comprising an antihistamine in a therapeutically effective amount for treating the allergy condition in the human having the allergy condition. The composition may further comprise an anti-drying composition comprising at least one of xylitol, erythiritol, mannitol, maltitol, tibitol, arabitol, ribose, and xylose in one or more therapeutically effective amounts for reducing nasal dryness caused by the allergy treatment composition. The composition may be delivered into at least one of the human's nose, eyes, mouth, and throat.

9 Claims, 1 Drawing Sheet

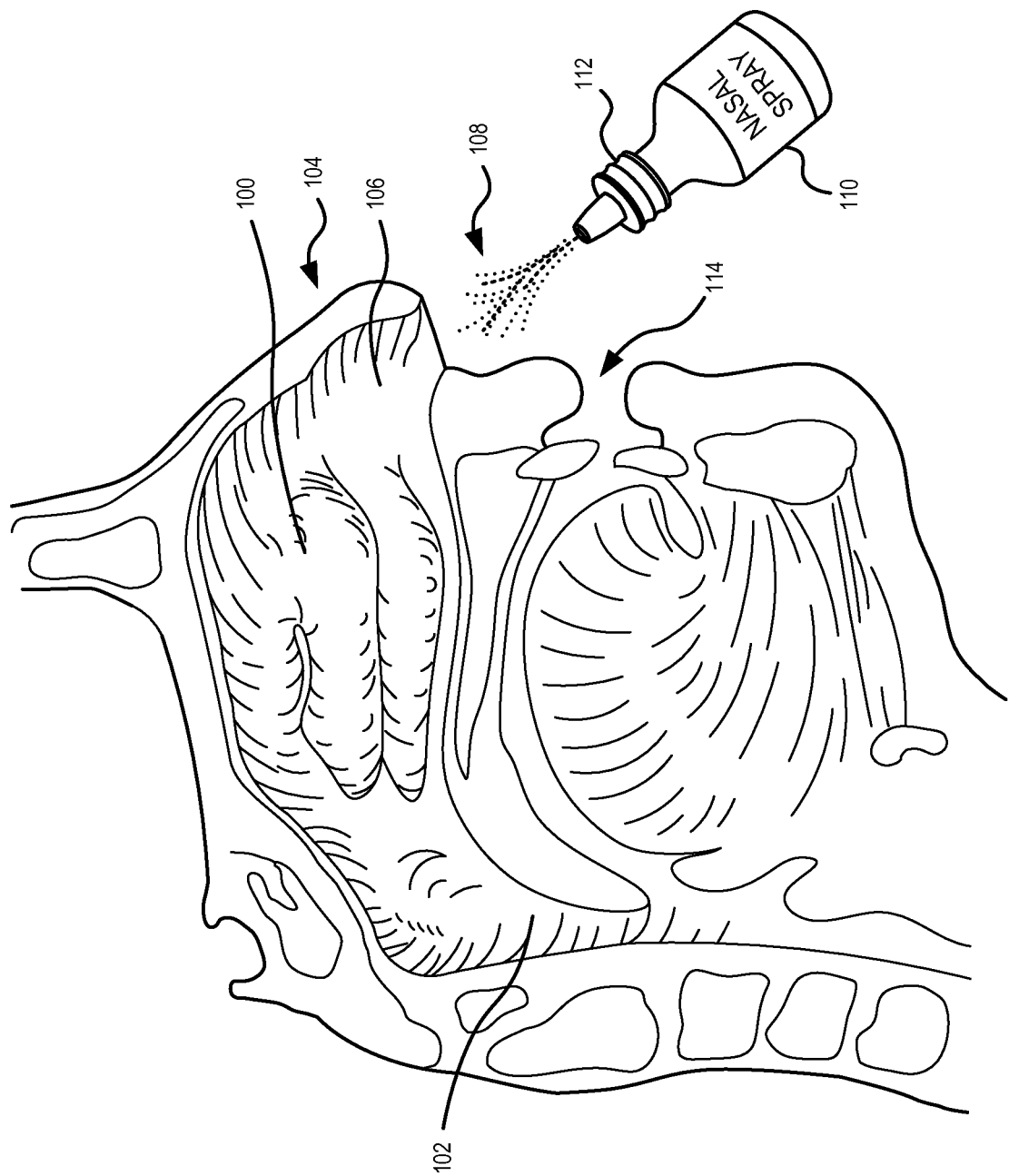

US 9,011,941 B2

COMBINED ALLERGY TREATMENT AND ANTI-DRYING COMPOSITIONS AND RELATED METHODS

RELATED APPLICATIONS

This application is a continuation of U.S. Patent Application Serial No. 13/903,860 titled "XYLITOL-BASED ANTI-MUCOSAL COMPOSITIONS AND RELATED METHODS AND COMPOSITIONS" filed on May 28, 2013, which claims priority from U.S. Provisional Patent Application No. 61/651,741 titled "XYLITOL-BASED ANTI-MUCOSAL COMPOSITIONS AND RELATED METHODS AND COMPOSITIONS," filed on May 25, 2012, each of which is incorporated herein by reference in its entirety.

SUMMARY

Disclosed herein are examples of embodiments and implementations of compositions and methods for alleviating an allergy condition while also reducing a drying effect of an allergy medication or other anti-mucosal composition.

In some embodiments, a nasal solution for alleviating an allergy condition may comprise an anti-mucosal composition in an amount effective for treating an allergy condition and at least one of xylitol and xylose in an amount effective for reducing nasal dryness caused by the anti-mucosal composition. The anti-mucosal composition may comprise at least one of an antihistamine, a nasal steroid, cromolyn sodium, phenylephrine hydrochloride, oxymetazoline hydrochloride, azelastine HCL, mometasone furoate, and a decongestant. The anti-mucosal composition may alternatively comprise a natural antihistamine, such as echinacea, chamomile, and/or basil.

The nasal solution may comprise a nasal spray, and may further comprise a nasal spray bottle configured to deliver the nasal solution. Alternatively, the nasal solution may comprise a nasal dropper configured to deliver the nasal solution in a liquid drop form.

In another example of a composition for alleviating an allergy condition, the composition may comprise an anti-mucosal composition in an amount capable of reducing the symptoms of an allergy condition, wherein the anti-mucosal composition comprises a drying agent effective for resulting in a drying effect on at least one of a typical user's nose, eyes, mouth, and throat. The composition may further comprise at least one of a polysaccharide, a monosaccharide, and a sugar alcohol configured to counteract the drying effect and in an amount effective for reducing the drying effect of the drying agent. The at least one of a polysaccharide, a monosaccharide, and a sugar alcohol may comprise at least one of xylitol, erythritol, xylose, mannitol, maltitol, ribitol, arabitol, and ribose.

In some embodiments, the composition may comprise a nasal solution. In such embodiments, the nasal solution may comprise a nasal spray, and may further comprise a nasal spray bottle configured to deliver the nasal solution. In other embodiments, the nasal solution may comprise a gel.

In some implementations of methods for treating an allergy condition and simultaneously reducing the drying effect of an allergy treatment agent, the method may comprise identifying a subject having an allergy condition and providing a solution. The solution may comprise an anti-mucosal composition comprising an allergy treatment agent in an amount effective for treating the allergy condition and at least one of xylitol and xylose in an amount effective for reducing the drying effect of the allergy treatment agent. Such methods may further comprise delivering the solution into at least one of the subject's nose, eyes, mouth, and throat.

In some implementations, the solution may comprise a nasal solution, and, in such implementations, the step of delivering the solution may comprise delivering the nasal solution into the subject's nose.

The allergy treatment agent may comprise at least one of an antihistamine, a nasal steroid, cromolyn sodium, phenylephrine hydrochloride, oxymetazoline hydrochloride, azelastine HCL, and mometasone furoate. The solution may comprise an aqueous solution or a gel. In implementations in which the solution comprises a gel, the step of delivering the solution may comprise delivering the gel using an adhesion delivery method. The gel may comprise a bio-adhesive agent in some implementations.

BRIEF DESCRIPTION OF THE DRAWINGS

The written disclosure herein describes illustrative embodiments that are non- limiting and non-exhaustive. Reference is made to certain of such illustrative embodiments that are depicted in the figures, in which:

FIG. 1 illustrates intranasal delivery of an anti-mucosal composition including xylitol consistent with embodiments of the present disclosure.

DETAILED DESCRIPTION

Anti-mucosal compositions, including antihistamines, are widely used to alleviate allergy symptoms such as itching and a runny nose. Antihistamines may prevent histamines produced by the body's immune response from attaching to histamine receptors in the nose and/or throat, thereby reducing allergy systems. Blocking this histamine response, however, has certain undesirable side effects. For example, administration of antihistamines and/or other anti-mucosal compositions may cause an individual's nasopharynx, nose, and/or throat to become uncomfortably dry and such dryness may lead to further conditions and/or complications.

For purposes of the disclosure contained herein, an "anti-mucosal" composition includes any composition that decreases the production or presence of mucous, including but not limited to antihistamines, nasal steroids, cromolyn sodium, phenylephrine hydrochloride, oxymetazoline hydrochloride, azelastine HCL, mometasone furoate, decongestants, and natural antihistamines and decongestants, such as echinacea, chamomile, and basil.

Consistent with embodiments disclosed herein, certain polysaccharides, monosaccharides, polysaccharides, or sugar alcohols, such as xylitol, may be administered in conjunction with anti-mucosal compositions to alleviate at least some of the negative side effects of the anti-mucosal compositions. For example, in certain embodiments, administering anti-mucosal compositions in conjunction with xylitol may reduce dryness associated with the use of the anti-mucosal compositions in an individual's nasopharynx, nose, and/or throat that would normally otherwise be associated with use of the anti-mucosal composition alone. In some embodiments, polysaccharides, monosaccharides and/or sugar alcohol compositions utilized in the anti-mucosal compositions disclosed herein may be prepared, at least in part, utilizing methods disclosed in U.S. Pat. Nos. 6,054,143 and 6,258,372, both titled "XYLITOL NOSE SPRAY" and U.S. Pat. No. 6,599,883 titled "NASAL DELIVERY OF XYLITOL," each of which is hereby incorporated by reference in its entirety.

Xylitol in particular has been shown to be very effective in moisturizing nasal passages and the like. Without being limited by theory, this is thought to occur because xylitol can create a hyper-osmotic solution that pulls moisture towards it from surrounding tissues without generated mucous. Thus, the combination of xylitol, or other similar compositions disclosed herein, and anti-mucosal agents, results in a decrease in mucous production without the accompanying dryness that typically accompanies antihistamines and other anti-mucosals, along with the accompanying anti-bacterial and other health benefits associated with xylitol and other similar agents.

Certain polysaccharides, monosaccharides, or sugar alcohols, including xylitol, have other beneficial properties aside from reducing dryness in the nasopharynx, nose, and/or throat. For example, regular consumption of xylitol has been shown to reduce the incidence of dental caries. This benefit is at least in part attributed to xylitol's ability to inhibit and/or reduce the growth and acid production of Streptococcus mutans, an important bacterium involved in the pathomechanism of dental caries. Xylitol may similarly inhibit the growth of Streptococcus pneumonia in vitro during its logarithmic growth phase. Streptococcus pneumonia is attributed to causing several harmful conditions, including certain types of pneumonia, upper respiratory infections, sinus infections, and other infectious diseases, including meningitis, sepsis, and acute otitis media episodes. Accordingly, administering xylitol in conjunction with anti-mucosal compositions may also help prevent and/or alleviate such other harmful conditions.

As detailed above, polysaccharides, monosaccharides and/or sugar alcohols utilized in the anti-mucosal compositions disclosed herein may include xylitol. Other exemplary polysaccharides, monosaccharides and/or sugar alcohols suitable for use in the anti-mucosal compositions disclosed herein may include, for example, erythritol, xylose, mannitol, maltitol, ribitol, arabitol, and/or ribose. Any other suitable polysaccharides, monosaccharides, and/or sugar alcohols that, when administered, reduce side effects associated with anti-mucosal compositions may also be utilized in other embodiments.

Anti-mucosal compositions including one or more polysaccharides, monosaccharides, and/or sugar alcohols may be delivered via an intranasal pathway. For example, an anti-mucosal composition including one or more polysaccharides, monosaccharides, and/or sugar alcohols may be delivered to an individual's nasopharnyx via a nasal spray. FIG. 1 illustrates intranasal delivery of an anti-mucosal composition including one or more polysaccharides, monosaccharides, and/or sugar alcohols 108 consistent with embodiments disclosed herein.

Anatomically, the nasopharynx 100 is a point at which the nasal passages 106 merge into one. It is also where the floor of the nose 104 bends downward with the superior-posterior surface of the palate. The openings of the auditory tubes (i.e., eustachian tubes) and the posterior nasal apertures (i.e., choanae) are located within the nasopharynx 100. The oropharynx 102 is located inferior to the nasopharynx 100 and is behind the mouth 114. By virtue of the anatomic locations of the eustachian tube openings in the nasopharynx 100, nasal administration of a solution, suspension, gel or powder may result in a more effective exposure of the eustachian tube openings versus administration via an oral route. Accordingly, administering anti-mucosal compositions including one or more polysaccharides, monosaccharides and/or sugar alcohols 108 via an intranasal pathway may be more effective than other routes of administration (e.g., orally, topically). However, it is anticipated that in other embodiments and implementations, one or more of the compositions disclosed herein may alternatively be administered orally by way of drops, a spray, a gel, a solution, or the like.

In certain embodiments, administering anti-mucosal compositions including one or more polysaccharides, monosaccharides, and/or sugar alcohols 108 via an intranasal pathway may be performed utilizing a nasal spray bottle 110. The nasal spray bottle 110 may any suitable bottle configured to retain anti-mucosal compositions including one or more polysaccharides, monosaccharides, and/or sugar alcohols 108 and to distribute (e.g., spray) the anti-mucosal compositions including one or more polysaccharides, monosaccharaides, and/or sugar alcohols 108 into an individual's intranasal pathway and/or nasopharynx 100 using a pump mechanism 112. Alternatively, the composition may be delivered from other nasal spray bottles by simply squeezing the bottle. In certain embodiments, the anti-mucosal compositions including one or more polysaccharides, monosaccharides, and/or sugar alcohols 108 may be stored in the nasal spray bottle 110 in liquid or powder form, and may be distributed into the intranasal pathway and/or nasopharnyx 100 as an aerosol.

In some embodiments, the anti-mucosal compositions including one or more polysaccharides, monosaccharides, and/or sugar alcohols 108 may be administered using a bathing delivery method. A bathing delivery method may utilize a solution comprising the anti-mucosal compositions including one or more polysaccharides, monosaccharides, and/or sugar alcohols 108 contained within a dilute (e.g., a less viscous, more fluid composition) pharmaceutically acceptable carrier suitable for nasal administration. For example, the anti-mucosal compositions including one or more polysaccharides, monosaccharides and/or sugar alcohols 108 may be contained within an aqueous solution including water and/or other pharmaceutically-acceptable carrier components. In certain embodiments, the composition may comprise approximately 0.1% saturation of a suitable aqueous solution. In certain embodiments, the composition may comprise approximately 1-15% of a suitable aqueous solution. The compositions may also comprise one or more polysaccharides, monosaccharides, and/or sugar alcohols 108, although other aqueous solution compositions are also contemplated. Some embodiments may comprise xylitol in an amount of between about 10 g/ml and about 60 g/ml.

The bathing delivery method may directly deliver the composition including one or more polysaccharides, monosaccharides, and/or sugar alcohols 108 to the nasopharynx 100 in conjunction with subsequent bathing of the nasopharyngeal area. As discussed above, this may be achieved using a nasal spray bottle 110. However, in alternative implementations, the composition may be delivered using alternative delivery mechanisms, such as droppers, misters, atomizers, brushes, swabs, etc. In some embodiments, utilizing a free-flowing, low viscosity aqueous solution may allow for a rapid and concentrated application of the composition.

In further embodiments, the anti-mucosal compositions including one or more polysaccharides, monosaccharides, and/or sugar alcohols 108 may be administered using an adhesion delivery method. An adhesion delivery method may utilize a more viscous solution, such as a gel, to deliver the anti-mucosal compositions including one or more polysaccharides, monosaccharides, and/or sugar alcohols 108. In certain embodiments, the viscous solution may include a bio-adhesive agent. An adhesion delivery method may rely on the adhesion of a solution containing the anti-mucosal compositions including one or more polysaccharides, monosaccharides, and/or sugar alcohols 108 to the nasal mucous membrane and a slow migration of the solution to the nasopharyngeal area. Utilizing a more viscous solution may provide for a more gradual and steady application of the composition to desired areas, such as within the nasal cavity, and may also increase the duration of the positive benefits of the composition, such as by decreasing the rate at which the composition is removed from the desired areas.

In certain embodiments, a solution including anti-mucosal compositions and one or more polysaccharides, monosaccharides, and/or sugar alcohols 108 may include a buffer, a thickening agent, a bio-adhesive, and/or a humectant. A pharmaceutically acceptable surfactant and a preservative may also be included along with one or more excipients suitable for a pharmaceutical composition.

In embodiments including a buffer, the buffer may be configured to maintain a pH level of the solution. Exemplary suitable buffers include acetate, citrate, and phosphate buffers. The thickening agent may include, for example, one or more of methylcellulose, xanthan gum, carboxyl methylcellulose, polyvinyl alcohol, hydroxypropyl cellulose, carbomer, starches, chitosans, acrylates, and mixtures therefore. In certain embodiments, these substances may also act as suitable bio-adhesives. Suitable exemplary humectants include sorbitol, propylene glycol, glycerol, and/or any combination thereof. Suitable surfactants may be anionic, cationic, or nonionic, and may include polyoxyethylene derivatives, fatty acids, and/or partial esters of sorbitol anhydrides. For example, the surfactant may include sodium lauryl sulfate, polysorbate 80, polyoxyl Stearate, polyoxy ethylene 50, fusieates, bile salts, and octoxynol. However, it should also be understood that many embodiments of the compositions disclosed herein will not need to include a buffer.

It will be understood by those having skill in the art that changes may be made to the details of the above-described embodiments without departing from the underlying principles presented herein. For example, the anti-mucosal compositions including one or more polysaccharides, monosaccharides, and/or sugar alcohols 108 disclosed herein may be administered via liquid drops from a dropper, topically (in some cases using a cotton swab or the like), orally, via a mister or atomizer, and/or via any other suitable manner of administration. In addition, any suitable combination of various embodiments, or the features thereof, is contemplated.

Any methods disclosed herein may comprise one or more steps or actions for performing the described method. The method steps and/or actions may be interchanged with one another. In other words, unless a specific order of steps or actions is required for proper operation of the embodiment, the order and/or use of specific steps and/or actions may be modified. It should also be understood that some implementations can be practiced without some or all of the steps disclosed herein. In addition, the steps of a method do not necessarily need to be executed in any specific order, or even sequentially, nor need the steps be executed only once, unless otherwise specified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein. The scope of the present invention should, therefore, be determined only by the following claims.

The invention claimed is:

1. A method for treating an allergy condition in a human, the method consisting essentially of the steps of:
   identifying a human having an allergy condition; and
   administering to the human having an allergy condition a composition consisting essentially of therapeutically effective amounts of at least one of cromolyn sodium, phenylephrine hydrochloride, oxymetazoline hydrochloride, azelastine hydrochloride, and mometasone furoate to treat said allergy condition in the human having an allergy condition, the composition further consisting essentially of therapeutically effective amounts of at least one of xylitol, erythiritol, mannitol, maltitol, tibitol, arabitol, ribose, and xylose in an amount effective for reducing nasal dryness caused by the at least one of cromolyn sodium, phenylephrine hydrochloride, oxymetazoline hydrochloride, azelastine hydrochloride, and mometasone furoate for treating the allergy condition.

2. The method of claim 1, wherein the composition is in an aqueous solution.

3. The method of claim 1, wherein the step of administering to the human having an allergy condition is via delivering the composition into at least one of the human's nose, eyes, mouth, and throat.

4. The method of claim 1, wherein the composition is a nasal solution.

5. The method of claim 4, wherein the step of administering to the human having an allergy condition is via delivering the nasal solution into the human's nose.

6. The method of claim 4, wherein the composition is a gel.

7. The method of claim 6, wherein the step of administering to the human having an allergy condition via delivering the gel using an adhesion delivery method.

8. The method of claim 1, wherein the step of administering to the human having an allergy condition is via at least one of a nasal spray bottle, a dropper, a mister, an atomizer, a brush, and a swab.

9. The method of claim 8, wherein the composition is a free-flowing, low viscosity aqueous solution.

* * * * *